(12) United States Patent
Modi

(10) Patent No.: US 7,140,761 B2
(45) Date of Patent: Nov. 28, 2006

(54) APPLICATION HANDPIECE WITH LAMP OF NOVEL SHAPE

(75) Inventor: Stefano Modi, Firenze (IT)

(73) Assignee: EL. EN S.P.A. (IT)

( * ) Notice: Subject to any disclaimer, the term of this patent is extended or adjusted under 35 U.S.C. 154(b) by 120 days.

(21) Appl. No.: 10/474,190

(22) PCT Filed: Apr. 3, 2002

(86) PCT No.: PCT/IT02/00209

§ 371 (c)(1),
(2), (4) Date: Oct. 2, 2003

(87) PCT Pub. No.: WO02/082866

PCT Pub. Date: Oct. 17, 2002

(65) Prior Publication Data

US 2004/0100798 A1   May 27, 2004

(30) Foreign Application Priority Data

Apr. 5, 2001  (IT) ............................. FI2001A0059

(51) Int. Cl.
 *F21V 29/00* (2006.01)
(52) U.S. Cl. ........................ 362/580; 362/264; 362/572
(58) Field of Classification Search ........ 362/263–265, 362/216, 294, 370, 259, 580, 572–575, 804; 606/1–26
See application file for complete search history.

(56) References Cited

U.S. PATENT DOCUMENTS

| 1,472,779 | A | * | 11/1923 | Anderson ..................... 607/80 |
| 2,261,215 | A | * | 11/1941 | Bird ........................ 250/504 H |
| 2,705,290 | A | * | 3/1955 | Newman .................. 250/493.1 |
| 4,229,658 | A | * | 10/1980 | Gonser .................... 250/504 R |
| 4,595,838 | A | | 6/1986 | Kerschgens ............. 250/504 R |
| 4,767,193 | A | * | 8/1988 | Ota et al. .................... 362/217 |
| 5,001,608 | A | | 3/1991 | Kehrli et al. ................. 362/19 |
| 5,405,368 | A | * | 4/1995 | Eckhouse .................... 607/88 |
| 6,177,678 | B1 | * | 1/2001 | Brass et al. .............. 250/461.1 |
| 6,235,016 | B1 | | 5/2001 | Stewart .......................... 606/9 |
| 6,758,845 | B1 | * | 7/2004 | Weckwerth et al. ........... 606/9 |

FOREIGN PATENT DOCUMENTS

| DE | 200 14 735 | 11/2000 |
| EP | 0 026 239 | 4/1991 |
| EP | 0 784 997 | 7/1997 |
| FR | 2 639 834 | 6/1990 |
| JP | 02159207 | 6/1990 |
| WO | WO 99/37271 | 7/1999 |

* cited by examiner

*Primary Examiner*—Alan Cariaso
*Assistant Examiner*—Bao Q. Truong
(74) *Attorney, Agent, or Firm*—McGlew & Tuttle, PC

(57) ABSTRACT

An essentially u-shaped discharge lamp (13) comprises a gaz fill and a pair of electrodes (15) at its ends. The lamp (13) way be comprised in a handpiece (1) for treating a surface by means of electromagnetic radiation.

21 Claims, 1 Drawing Sheet

US 7,140,761 B2

APPLICATION HANDPIECE WITH LAMP OF NOVEL SHAPE

TECHNICAL FIELD

The present invention relates to an application handpiece and a lamp for said handpiece, designed for use in equipment for medical and cosmetic treatment, and also for all applications in which a flash lamp source with the smallest possible lateral dimension has to be used in the proximity of the surface to be treated.

The lamp is a source of photons which, with suitable intensity and time-based delivery control laws, can be used for action on the human body, for example depilation, by causing irreversible damage to the follicle and hair bulb, or other treatments which require high densities of light energy on the treated surface.

BACKGROUND OF THE INVENTION

At the present time, techniques of removing excess hair are no longer applicable solely to women with problems of hirsutism or hypertrichosis, but are commonly practiced on patients of both sexes, who are not necessarily suffering from specific diseases, but may require treatment for purely cosmetic purposes. The procedures commonly used for this purpose can be classified according to the duration of the results. According to this classification, there are short-term systems (razors, tweezers, cold and hot waxing, creams, gels and electrical depilators), and long-term systems which, after a certain number of sessions, can even yield permanent results. Some examples of this second group of systems are electrocoagulation needles, radio frequency scalpel needles, non-coherent light and lasers. Among the long-term treatment methods, the greatest success has been obtained with the use of systems based on the theory of selective photothermolysis, which cause damage to the hair bulb by means of the electromagnetic energy absorbed by the melanin present in the hair or by the hemoglobin of the follicle blood vessels.

Non-coherent light and laser depilation systems are more effective when they strike the hair in the growth phase ("anagen"). The growth of hair is not continuous, but cyclical: a rest period called "telogen" follows each growth period called "anagen"; the transition period between the two phases is known as "catagen". The duration of the cycle is different in the different regions, varying from 2–6 years for the head hair to only 4–8 weeks for the eyebrows. According to current biological models, the cells giving rise to the follicle are located in what is known as the "bulge area". These cells form the new hair matrix, thus initiating the growth phase. In the initial part of this phase, when the follicle is shorter, the papilla is closer to the skin surface; subsequently it increases its length, proliferating for a period which varies according to the anatomical location. It is in the initial phase of anagen, or anagen 1, that the "target" structures of the follicle (such as the papilla and the bulge area) with its vascular system are closer to the hair and to the skin surface; as the papilla and the end part of the hair become closer, there is a greater probability that the "light" energy absorbed by the melanin of the skin, and that which arrives directly, will cause irreparable damage to the papilla, permanently blocking its ability to make a hair grow. From what has been stated above, it is evident why the action of a "photodepilation" system is more effective in the anagen phase.

In a non-coherent light depilation system, use is made of a discharge lamp, normally consisting of a cylindrical container of material which is transparent to the electromagnetic radiation in the visible band and in the near infrared. Inside the container, at a suitable pressure, there is a pure gas or a mixture of gases, according to the characteristics to be obtained for the emitted light spectrum. At the ends of the container there are two electrodes, positioned in glass-metal seals so that one end of each electrode faces the internal environment, where the desired gaseous atmosphere has been created, while the other end forms an externally accessible current lead for the electrical power supply. The structure of the discharge lamp is typically rectilinear. When the lamp is excited by suitable levels of voltage and current, according to time-based control laws, a discharge is initiated in the mixture contained in it, generating the emission of the radiation. The lamp has to be very close to the skin, or more generally close to the surface to be treated, in order to obtain the maximum intensity. To maximize the effectiveness of the treatment, the handpiece must not mask any part of the surface to be treated with portions, such as the electrodes and current leads, which are not active because they do not emit radiation. A good illustration of this point is provided by the depilatory application. In this case, the irradiation of the skin must be carried out in a uniform way, in order to avoid having untreated areas or areas in which treatment is repeated, especially in adjacent areas affected by two successive treatments. In other words, the operator must take great care when maneuvering the application unit containing the lamp, in order to provide continuity of treatment in the areas adjacent to the area concerned. It is therefore very important for the operator to have a full view of the portion of skin or other surface concerned on which the radiation is to be made to act, wherever the application unit is positioned.

The conventional structure of the lamps described above does not allow the irradiated portion to be viewed satisfactorily, since the application handpiece has two inactive areas, namely the parts occupied by the electrodes and by the current leads, where there is no discharge and consequently no emission of radiation.

To overcome this problem of masking by inactive parts, application handpieces have been developed with conventional lamps, in which optical guide structures are placed in the emitting region of the lamp to guide the light towards the surface to be treated, thus enabling the light source to be moved away from said surface. However, these handpieces are of complicated design, and do not fully overcome the aforementioned problems.

OBJECTS AND SUMMARY OF THE INVENTION

The object of the present invention is to provide a lamp and an application handpiece which overcome the aforesaid problems in an effective way.

These objects are achieved with a lamp as claimed in claim 1 and with a handpiece as claimed in claim 5. Further possible advantageous characteristics of the handpiece and of the lamp are indicated in the dependent claims.

Essentially, according to the invention, the structure of the lamp is modified by changing the conventional cylindrical structure with a rectilinear axis to a C- or U-shaped structure, preferably with a central portion which is still cylindrical with a rectilinear axis, but with the two terminal portions, in which the electrodes are fitted, bent back, preferably at 90°. There is no reason why the lamp should not have a curved axis in the intermediate area, but the rectilinear form is preferable because of its greater uniformity of irradiation and the reduction in dimensions which can be obtained.

In practice, the bending of the terminal portions can be made to start at the ends of the light-emitting discharge, in other words at the ends of the electrodes; alternatively, the bending can start in the portion in which there is still emission of light, but with a sacrifice of only a length of each of the two terminal portions equal to the diameter of the structure itself, so that the discharge starts in the two bent terminal portions with the end result of a greater uniformity of emission by the rectilinear area. In this case, the electrodes terminate before the area in which the terminal portions are joined to the central rectilinear portion.

With these new types of lamp, it is possible to produce an application handpiece which has a contact surface equal or approximately equal to the area to be treated. This smaller surface is the only surface which has to be applied to the surface to be treated, and allows the operator to juxtapose the treated portions accurately because of the full view of the operating site. The advantages of this solution over those known up to the present time, which use handpieces with rectilinear lamps, are:

a reduction in the lateral dimension and consequently the achievement of a better view of the surface to be treated and better handling qualities of the handpiece;
 the reduction of the distance between the lamp and the surface to be treated makes it possibly to shorten the light guide which is normally provided at the window of the handpiece from which the electromagnetic radiation is emitted;
 the shortening of the light guide permits a reduction of absorption losses in said guide;
 the shortening of the light guide makes it possible to cool the treated surface effectively by means of the lamp cooling liquid.

Furthermore, the physical dimensions of the handpiece and its weight are much smaller, for a given treated area, than those of other systems based on conventional lamps. Additionally, the light guide, being of limited thickness, remains entirely inside the handpiece. This ensures that, when the lamp emits light energy, this energy remains confined virtually completely in the treated area, thus reducing to a minimum the lateral emission which tends to dazzle the operator, a problem that typically arises in systems with a light guide which projects from the handpiece.

The handpiece according to the invention comprises a pair of electrical connections for the lamp and a housing compartment for said lamp, said compartment having a window for the output of the electromagnetic radiation generated by said lamp. Characteristically, the electrical connections are placed side by side and are positioned on the same side of the housing compartment. The connections are preferably parallel to each other, but this is not essential. The orientation of the connections with respect to each other depends on the shape of the lamp.

The placing of the connections on the same side of the electromagnetic radiation output window provides a particularly advantageous configuration of the handpiece, enabling the aforementioned advantages to be obtained. In practice, the electrical connections are placed—with respect to said housing compartment—in a position opposite said window. The position can be such that the lamp lies in a plane orthogonal to the plane of the radiation output window. However, this is not an essential condition, although it is preferred. This is because the lamp can also be positioned in a plane which is inclined with respect to the window, although the orthogonal position provides an additional reduction in the overall dimensions of the handpiece.

The lamp is a discharge lamp and is essentially U-shaped.

In the preceding and following text, specific reference is made to depilation, but in fact the lamp and the handpiece according to the invention have other medical and cosmetic applications (for example, the treatment of vascular skin lesions such as port wine stain, hemangioma and telangiectasis), in addition to applications in the industrial field, for example in processes of drying, polymerization, etc.

BRIEF DESCRIPTION OF THE DRAWINGS

The invention will be more clearly understood from the description and the attached drawing, which shows a practical, non-limiting example of the invention. In the drawing.

DETAILED DESCRIPTION OF THE PREFERRED EMBODIMENT OF THE INVENTION

Figure 1:
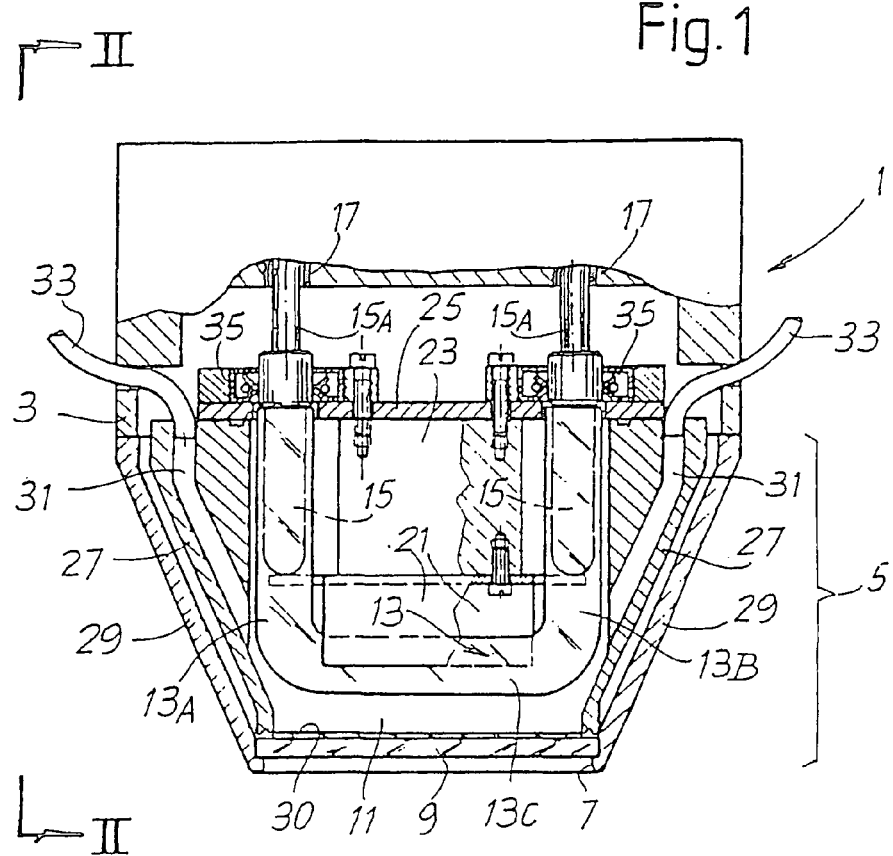
FIG. 1 shows a partial section through a median plane of the handpiece according to the invention with the lamp fitted into the handpiece.
Figure 2:
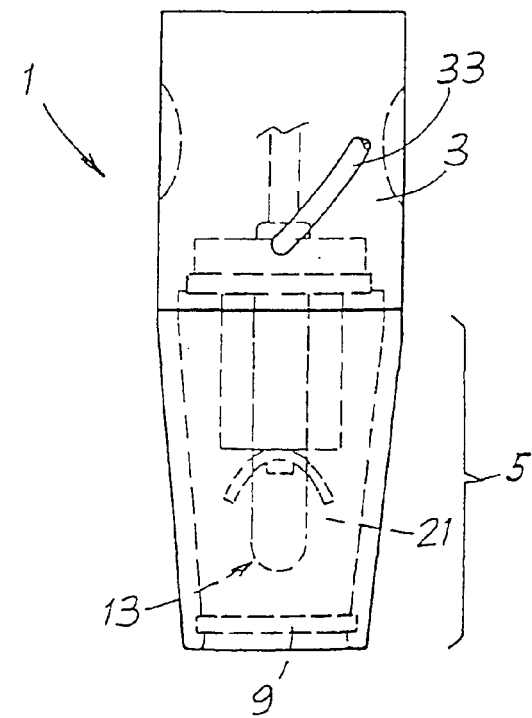
FIG. 2 shows a view along to II—II in FIG. 1.

In FIG. 1, the number 1 indicates in a general way a handpiece constructed according to the invention. The handpiece 1 has a first portion 3 forming the handle and a second portion 5 integral with the portion 3 and extending therefrom with a tapered shape terminating in a window 7 filled with a light guide 9.

A compartment 11, in which a lamp 13 is housed, is formed in the tapered portion 5 of the handpiece 1. The lamp is U-shaped, with an essentially rectilinear and cylindrical central portion 13C, to which are joined two terminal portions 13A and 13B, into which the electrodes 15 are fitted. These electrodes, on which a seal is made by the glass forming the container that constitutes the lamp, project from the container formed by the portions 13A, 13B and 13C, to provide current leads 15A for connection to a pair of electrical connections provided in the upper portion 3 of the handpiece 1. The electrical connections, indicated schematically by 17, into which the current leads 15A are fitted, are parallel to each other, as are the electrodes 15, and are placed on the same side of the compartment 11 in which the lamp is housed. However, the parallel arrangement of the connections 17 is not essential. The lamp could also have portions 13A and 13B converging on each other, in which case the connections would not be parallel. Additionally, in the illustrated example the lamp is shown lying in a plane orthogonal to the plane of the light guide 9. This is the optimal configuration, but there is no reason why the plane in which the lamp lies should not be inclined with respect to the light guide 9.

A reflector, indicated schematically by 21, is supported by a block 23 and is positioned within the lamp housing compartment 11. The reflector 21, which has a suitable shape (with a parabolic cross section, for example), reflects the radiation generated by the discharge lamp 13 towards the window filled with the light guide 9.

The block 23 is carried by a plate 25 fixed laterally to tapered lateral walls 27. The plate 25 and the block 23 can also consist of a single component. Within the components 27 there are formed ducts 31 which open into the compartment 11 in which the lamp is fitted, and which are connected at their tops to tubes 33 for the introduction of a lamp cooling fluid circulating in a heat dissipation system external to the handpiece and comprising for example a heat exchanger and/or a cooling battery. The portion 5 of the handpiece is completed and sealed with a cover 29 of plastic or other material, which is carried on the front of the window with the light guide 9. A seal is formed around the light guide by means of a gasket 30 between the light guide 9 and the front edge of the walls 27, onto which the light guide is pressed. The light guide is housed completely within the cover 29 which has a rectangular housing forming the window for the output of the electromagnetic radiation generated by the lamp 13. Thus the light radiation emitted by the lamp does not escape laterally from the handpiece when the latter is applied to the surface to be treated, except in wholly negligible amounts.

A fluid, typically water, is made to circulate in the compartment 11 by means of the ducts 31, to remove the heat generated by the discharge lamp 13, and this can also have the function of cooling the tissue or more generally the surface being treated. The components 27 and the compartment [lacuna]

Annular gaskets 35 are placed above the plate 25 to prevent the escape of cooling liquid toward the electrical connections 17.

The connections 17 are connected to electrical wires, not shown, which pass out of the handpiece in a cord which also contains the tubes 33 for the supply of the cooling fluid.

As clearly shown in FIG. 1, the U-shaped configuration of the lamp 13, with its central rectilinear portion 13C joined to the terminal portions 13A and 13B, makes it possible to produce a handpiece having a specific shape which is tapered toward the window for the output of the radiation generated by the discharge lamp 13, in such a way that the operator can have a virtually complete view of the area to be treated, and can thus carry out more precise treatments, without either leaving areas untreated or treating the same area twice.

The arrangement of the electrodes 15 and the corresponding electrical connections 17 which are placed side by side, on the side opposite the window filled with the light guide 9, enables the light guide to be made with a shorter length, and therefore with reduced thickness. This yields the advantages indicated above.

It is to be understood that the drawing shows only an example provided solely as a practical demonstration of the invention, this invention being variable in its forms and arrangements without departure from the scope of the guiding principle of said invention.

The invention claimed is:

1. A handpiece for treating a surface by means of lamp-emitted electromagnetic radiation, comprising a grip portion for hand-gripping the handpiece and a pair of electrical connections for a lamp and a compartment for housing said lamp, said compartment having an elongated window for the output of the electromagnetic radiation generated by said lamp, wherein: said electrical connections are placed side by side and are positioned on the same side of the housing compartment, in a position opposite to said window, said connections being arranged at opposed ends of said windows; said compartment being designed to house an essentially U-shaped lamp having an essentially rectilinear central portion and two terminal portions with electrodes forming current leads by means of which said lamp is connected to said electrical connections, and said essentially rectilinear portion facing said window when the lamp is housed in said compartment, said lamp housing compartment being closed by said window to radiate said lamp evenly on a patient's skin surface and a duct being provided between said compartment and said window.

2. The handpiece as claimed in claim 1, including said lamp, wherein said lamp is a flash lamp.

3. The handpiece as claimed in claim 1, wherein said window is filled with a light guide.

4. The handpiece as claimed in claim 3, wherein said compartment for housing in the lamp is cooled by means of a cooling fluid.

5. The handpiece as claimed in claim 1, further characterized by said grip portion and a transition portion connected thereto, which is tapered, terminates with said output window and houses said lamp.

6. The handpiece as claimed in claim 4, further comprising:
   one or more ducts for the circulation of the cooling fluid, said ducts extending parallel to the tapered walls of said portion housing said lamp.

7. The handpiece as claimed in claim 1, wherein said electrical connections for the lamp are parallel to each other.

8. The handpiece as claimed in claim 7, wherein said connections for the lamp are orthogonal to the output window.

9. The handpiece as claimed in claim 1, wherein said lamp lies in a plane orthogonal to said window.

10. The handpiece as claimed in claim 6, wherein said electrical connections for the lamp are parallel to each other.

11. The handpiece as claimed in claim 10, wherein said connections for the lamp are orthogonal to the output window.

12. The handpiece as claimed in claim 6, wherein said lamp lies in a plane orthogonal to said window.

13. A handpiece for treating a surface by means of lamp-emitted electromagnetic radiation, comprising:
   a pair of electrical connections for the lamp and a compartment for housing a lamp, said compartment having an elongated window for the output of the electromagnetic radiation generated by said lamp, wherein said electrical connections are placed side by side and are positioned on the same side of the housing compartment, in a position opposite to said window, said connections being arranged at opposed ends of said windows; said compartment housing an essentially U-shaped lamp having an essentially rectilinear central portion and two terminal portions with electrodes forming current leads by which said lamp is connected to said electrical connections, said essentially rectilinear portion facing said window, a reflector being provided adjacent said lamp in a direction away from said window, said window being filled with a light guide, said compartment for housing the lamp being cooled by ducts carrying a cooling fluid.

14. The handpiece as claimed in claim 13, wherein said light guide is completely housed within a sealing cover of the handpiece.

15. A handpiece for treating a surface by means of lamp-emitted electromagnetic radiation, comprising:
   a pair of electrical connections for the lamp and a compartment for housing a lamp, said compartment having an elongated window for the output of the electromagnetic radiation generated by said lamp, wherein said electrical connections are placed side by side and are positioned on the same side of the housing compartment, in a position opposite to said window, said connections being arranged at opposed ends of said windows; said compartment being designed to house an essentially U-shaped lamp having an essentially rectilinear central portion and two terminal portions with electrodes forming current leads by means of which said lamp is connected to said electrical connections, said essentially rectilinear portion facing said window when the lamp is housed in said compartment;

a grip portion connected to said compartment for housing the lamp, said compartment for housing the lamp formed in a tapered portion of said grip portion, said lamp housing compartment being tapered in shape and terminating with said output window.

16. A handpiece for treating a surface by means of lamp-emitted electromagnetic radiation, comprising:

a pair of electrical connections for the lamp and a compartment for housing a lamp, said compartment having an elongated window with rectangular opening for the output of the electromagnetic radiation generated by said lamp, wherein said electrical connections are placed side by side and are positioned on the same side of the housing compartment, in a position opposite to said window, said connections being arranged at opposed ends of said windows; said compartment being designed to house an essentially U-shaped lamp having an essentially rectilinear central portion and two terminal portions with electrodes forming current leads by means of which said lamp is connected to said electrical connections, said essentially rectilinear portion facing said window when the lamp is housed in said compartment;

said window being filled with a light guide;

said tapered portion being delimited by a sealing cover provided with said window filled with said light guide, said cover pressing the light guide onto an inner wall delimiting said compartment for housing the lamp; and ducts for circulating cooling fluid, said ducts extending along a tapered wall into said compartment housing said lamp.

17. The handpiece as claimed in claim 16, wherein said cover has a housing in which the light guide is completely contained.

18. A handpiece for treating a surface by electromagnetic radiation, the handpiece comprising:

a gripping portion;

a lamp housing compartment rigidly connected to said gripping portion;

ducts extending into said lamp housing compartment to circulate a cooling fluid;

a U-shaped flash lamp characterized by a pulsed light source arranged in said lamp housing compartment, said lamp having a substantially rectilinear central portion and two terminal portions;

a pair of electrical connections for said lamp arranged in said compartment;

a window in said compartment for passing electromagnetic radiation generated by said lamp, said electrical connections and said window are designed and arranged such that said substantially rectilinear central portion of said lamp faces said window and extends substantially parallel to said window.

19. The handpiece in accordance with claim 18, further comprising:

a cooling liquid circulation system for cooling said lamp housing compartment.

20. The handpiece in accordance with claim 18, wherein:

said lamp housing compartment has a tapered portion ending with said output window.

21. A handpiece for treating a surface with electromagnetic radiation, the handpiece comprising:

a grip portion shaped to be gripped by a hand of an operator applying the electromagnetic radiation to a patient;

a lamp housing compartment connected to said grip portion, said lamp housing compartment including an elongated window with rectangular opening for passing electromagnetic radiation, said lamp housing compartment being formed in a tapered portion of said grip portion, said lamp housing compartment tapering in shape from said grip portion to said window;

a lamp characterized by a pulsed light source arranged in said lamp housing compartment, said lamp having a substantially rectilinear central portion facing said window and two terminal portions, said terminal portions being bent away from said from said central portion in a direction away from said window and toward said grip portion, a reflector being provided adjacent said lamp in said direction away from said window;

electrical connections arranged in one of said grip portion and said lamp housing portion, said electrical connections being connected to said terminal portions of said lamp, said electrical connections being arranged on a side of said lamp which is diametrically opposite said window, said lamp housing compartment being closed by said window to radiate said lamp evenly on a patient's skin surface and a duct being provided between said lamp housing compartment and said window.

* * * * *